US006258546B1

(12) United States Patent
McMillian et al.

(10) Patent No.: US 6,258,546 B1
(45) Date of Patent: Jul. 10, 2001

(54) DETECTION OF NUCLEIC ACID AMPLIFICATION

(75) Inventors: Ray A. McMillian, Timonium; Karen Eckert, Perry Hall; Donald W. Copertino, Catonsville; Tobin J. Hellyer, Owings Mills, all of MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/602,996

(22) Filed: Jun. 23, 2000

(51) Int. Cl.$^7$ ............................... C12Q 1/68; C12P 19/34
(52) U.S. Cl. ............................... 435/6; 435/91.2
(58) Field of Search ...................... 435/6, 91.2

(56) References Cited

U.S. PATENT DOCUMENTS

| | | | |
|---|---|---|---|
| 5,270,184 | 12/1993 | Walker et al. | 435/91.2 |
| 5,547,861 | 8/1996 | Nadeau et al. | 435/91.2 |
| 5,550,025 | 8/1996 | Walker | 435/6 |
| 5,567,583 * | 10/1996 | Wang et al. | 435/6 |
| 5,607,834 | 3/1997 | Bagwell | 435/6 |
| 5,919,630 | 7/1999 | Nadeau et al. | 435/6 |
| 5,928,869 | 7/1999 | Nadeau et al. | 435/6 |
| 5,958,700 | 9/1999 | Nadeau et al. | 435/6 |
| 6,022,686 * | 2/2000 | Garman et al. | 435/6 |

OTHER PUBLICATIONS

G. T. Walker et al. "Isothermal in vitro amplification of DNA by a restriction enzyme/DNA polymerase system" PNAS, vol. 89, pp. 392–396 (1992).*

* cited by examiner

Primary Examiner—Kenneth R. Horlick
Assistant Examiner—Teresa Strzelecka

(57) ABSTRACT

For use in nucleic acid amplification reactions, the detector oligonucleotides of the invention comprise a target binding sequence which is at least partially the same as the target binding sequence of an amplification primer present in the target amplification reaction, so that the detector oligonucleotide and the amplification primer compete for hybridization to the same sequence in the target. Hybridization of the amplification primer to the target upstream from the detector oligonucleotide generates a nickable restriction endonuclease recognition site. When this site is nicked and strand displacement occurs from the nick, both the 3' end of the amplification primer and the detector oligonucleotide are displaced. The displaced detector oligonucleotide may then be detected as an indication of the presence of the target sequence, for example by unfolding of a fluorescently labeled secondary structure present in the detector oligonucleotide to reduce fluorescence quenching.

23 Claims, 1 Drawing Sheet

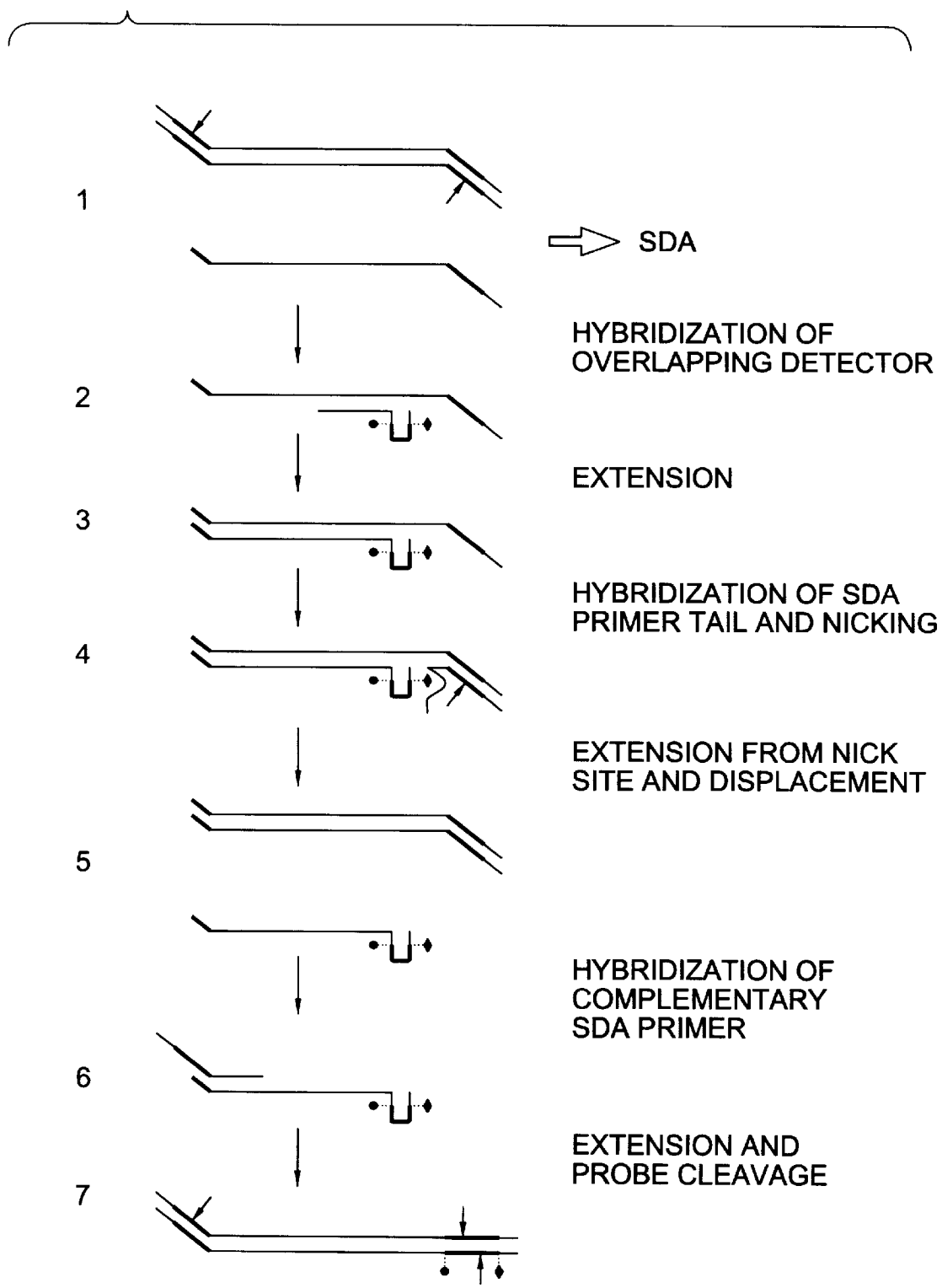

DETECTION OF NUCLEIC ACID AMPLIFICATION

FIELD OF THE INVENTION

The invention relates to methods for detecting the presence of nucleic acid target sequences, and in particular to detection of such target sequences in nucleic acid amplification reactions.

BACKGROUND OF THE INVENTION

Recent advances in oligonucleotide probe-based technologies have employed changes in fluorescence quenching and probes or primers comprising intramolecularly base-paired secondary structures for detection of nucleic acid target sequences. In these systems, a donor fluorophore and a quencher dye are in close proximity in the intramolecularly base-paired secondary structure in the absence of the target sequence but become spatially separated in the presence of target due to unfolding of the secondary structure. The separation of the two dyes reduces quenching of the donor fluorophore which may be detected as an increase in donor fluorescence. This indicates that the target is present and/or is being amplified. That is, the donor and acceptor are linked to a single, intramolecularly base-paired oligonucleotide such that there is a detectable difference in the fluorescence properties of one or both when the oligonucleotide is unhybridized vs. when it is hybridized to its complementary sequence. For example, a self-complementary oligonucleotide labeled at each end may form a hairpin which brings the two fluorophores (i.e., the 5' and 3' ends) into close proximity where energy transfer and quenching can occur. Hybridization of the self-complementary oligonucleotide to its complement on a second oligonucleotide disrupts the hairpin and increases the distance between the two dyes, thus reducing quenching. Hairpin structures labeled in this manner are described by Tyagi and Kramer (1996. *Nature Biotech.* 14, 303–308) and B. Bagwell, et al. (1994. *Nucl. Acids Res.* 22, 2424–2425; U.S. Pat. No. 5,607,834). In contrast, the secondary structure-containing detector oligonucleotides disclosed in U.S. Pat. No. 5,928,869 have the target binding sequence wholly or partially in a single-stranded "tail" region rather than fully contained within the intramolecularly base-paired secondary structure. The secondary structure (e.g., a hairpin) therefore need not unfold in order to initially hybridize to the target. Hybridization of the single-stranded tail is not competitive so the kinetics of the reaction favor hybridization to the target.

SUMMARY OF THE INVENTION

In one embodiment, the present invention employs detector oligonucleotides having structures similar to the signal primers described in U.S. Pat. No. 5,547,861 (the "'861 Patent") except that, in contrast to the '861 Patent, the detector oligonucleotides of the invention have target binding sequences which are at least partially identical to the target binding sequence of an amplification primer. That is, the hybridization site of the detector oligonucleotide of the invention overlaps the hybridization site of an amplification primer in the amplification reaction. Whereas the detector oligonucleotide and the amplification primer in the '861 Patent hybridize to the target sequence at the same time through their different target binding sequences, in the present invention their hybridization is competitive and essentially mutually exclusive with respect to the target binding sequences. Overlapping the hybridization sites of the detector oligonucleotide and the amplification primer allows the practitioner to use a single conserved sequence for both detection and amplification, which is an advantage in targets where conserved sequences are rare. The inventive methods also allow amplification of small targets which may not be long enough for specific hybridization of both the detector oligonucleotide and the amplification primer at the same time.

In another embodiment, the present invention provides methods for displacing oligonucleotides from target sequences wherein a first oligonucleotide is hybridized to the target sequence and a second oligonucleotide comprising a nickable RERS (restriction endonuclease recognition site) in single-stranded form is employed to generate a nickable double-stranded RERS upstream from the first oligonucleotide. Nicking with strand displacement from the nick displaces both the 3' end of the second oligonucleotide and the first, downstream oligonucleotide. If desired, the displaced first oligonucleotide may be used in subsequent reactions for detection of the target sequence.

DESCRIPTION OF THE DRAWINGS

FIG. 1 illustrates the use of the detector oligonucleotides of the invention in an amplification reaction for detection of target.

DETAILED DESCRIPTION OF THE INVENTION

The present invention employs detector oligonucleotides for detection of target sequences. Many of the features of the preferred detector oligonucleotides of the invention are described in the '861 Patent with reference to signal primers. They are typically about 10–60 nucleotides long and comprise a 3' target binding sequence and a 5' sequence which does not bind to the target. The nonbinding portion of the detector oligonucleotide includes a reporter group or label, or is a structural feature to facilitate detection or capture. However, the detector oligonucleotides of the invention comprise a target binding sequence which is at least partially the same as the target binding sequence of an amplification primer present in the target amplification reaction, so that the detector oligonucleotide and the amplification primer compete for hybridization to the same sequence in the target. Hybridization of the detector oligonucleotide and amplification primer target binding sequences are therefore essentially mutually exclusive in the present invention, in contrast to the '861 Patent where hybridization of these two primers occurs noncompetitively to two non-overlapping sequences in the target. Preferred detector oligonucleotides contain a donor/quencher dye pair linked such that fluorescence quenching occurs in the absence of target (see U.S. Pat. No. 5,928,869; the "'869 Patent"). Unfolding or linearization of an intramolecularly base-paired secondary structure in the detector oligonucleotide in the presence of the target increases the distance between the dyes and reduces fluorescence quenching. Unfolding of the base-paired secondary structure typically involves intermolecular base-pairing between the sequence of the secondary structure and a complementary strand such that the secondary structure is at least partially disrupted. It may be fully linearized in the presence of a complementary strand of sufficient length. In a preferred embodiment, there may be an RERS present between the two dyes such that intermolecular base-pairing between the secondary structure and a complementary strand also renders the RERS double-stranded and cleavable by a restriction endonuclease. Cleavage by the restriction endonuclease separates the donor and acceptor dyes onto separate nucleic acid fragments, further contributing to decreased quenching. In either embodiment, an associated change in a fluorescence parameter (e.g., an increase in donor fluorescence intensity, a decrease in acceptor fluorescence intensity or a ratio of fluorescence before and after unfolding) is monitored as a indication of the presence of the target sequence. Monitoring a change in donor fluorescence intensity is preferred, as this change is typically larger than the change in acceptor fluorescence intensity. Other fluorescence parameters such as a change in fluorescence lifetime may also be monitored.

The detector oligonucleotides of the invention are preferably used as signal primers for detection of target in an amplification reaction to generate detectable double-stranded secondary amplification products as described in the '861 and '869 Patents. The detector oligonucleotide signal primer reaction according to the invention is illustrated in FIG. 1, using SDA as an exemplary amplification reaction.

The detector oligonucleotides are included in an otherwise conventional SDA (Strand Displacement Amplification) reaction. In the reaction, target generation begins essentially as described in U.S. Pat. No. 5,270,184, with hybridization and extension of amplification and bumper primers, hybridization and extension of the opposite amplification and bumper primers on the displaced strand, and hybridization and extension of the opposite amplification primer on the second displaced strand to produce a double-stranded product bounded on each end by the sequences of the amplification primers. In SDA these terminal sequences include nickable restriction endonuclease recognition sites. FIG. 1 illustrates the reaction involving the detector oligonucleotides of the invention, beginning with the double-stranded product of target generation flanked by restriction endonuclease recognition sites (step 1). Nicking (arrows in step 1) and extension from the nick displaces a single-stranded molecule to which the detector oligonucleotide can hybridize (step 2) and be extended (step 3). As the resulting molecule has a single-stranded RERS at its 3' end, an amplification primer can hybridize through its RERS, but the hybridization site for the target binding sequence of the amplification primer is occupied by the detector oligonucleotide. This leaves the 3' end of the amplification primer unhybridized while rendering the RERS double-stranded and nickable (step 4). Nicking by the restriction endonuclease (arrows in step 4) and displacement by the polymerase not only displaces the 3' end of the amplification primer, it continues to displace the extended detector oligonucleotide (step 5). A complementary amplification primer can hybridize to the displaced, extended detector oligonucleotide (step 6) and be extended (step 7). If the detector oligonucleotide has a fluorescently labeled hairpin structure as the nonbinding reporter group, hybridization and extension of the complementary amplification primer on the displaced extended detector oligonucleotide unfolds the secondary structure, resulting in a reduction in fluorescence quenching as illustrated in FIG. 1. If the hairpin of the detector oligonucleotide also contains a cleavable RERS, cleavage further reduces fluorescence quenching (right-side arrows in step 7). The detected change in fluoresence serves as an indication that the target is present and has been amplified.

Because hybridization of the amplification primer and the detector oligonucleotide is competitive, it will be appreciated that an amplification primer may also hybridize to the displaced single-stranded molecule shown in step 1. If the amplification primer hybridizes before the detector oligonucleotide (not shown in FIG. 1), a nickable double-stranded RERS is produced at one end of the molecule which allows the molecule to be directly amplified by SDA ("→SDA" in step 1). Nicking and displacement from the nick during SDA serves to produce additional amplification products to which the detector oligonucleotide can ultimately hybridize to produce a signal indicating the presence of the target sequence.

The signal may be detected at a selected endpoint in the reaction. However, because displaced, extended detector oligonucleotides are produced concurrently with the target amplification, the signal may also be monitored as the reaction is occurring, i.e., in "real-time." Such homogeneous real-time assays can be used to provide semi-quantitative or quantitative information about the initial amount of target present. For example, the rate at which the signal is produced during the reaction is an indication of initial target levels. As a result, when more initial copies of the target sequence are present, the signal more rapidly reaches a selected threshold value (i.e., a shorter time to positivity). In addition, the rate of change in the signal during the course of the reaction is more rapid in samples containing higher initial amounts of target than in samples containing lower initial amounts of target (i.e., increased slope of the signal curve). These or other measurements as is known in the art may be made as an indication of the presence of target or an indication of target amplification. The initial amount of target is typically determined by comparison of the experimental results to results for known amounts of target.

It will also be appreciated that the overlapping target binding sequence of the amplification primer is necessary only for concurrent amplification of the target sequence. If only displacement of the downstream detector oligonucleotide is desired, the amplification primer target binding sequence can be eliminated, leaving only the single-stranded RERS. In this embodiment, once the nickable double-stranded RERS is generated, nicking and strand displacement from the nick result in displacement of both the 3' end of the RERS and the detector oligonucleotide. The displaced, extended detector oligonucleotide may then be used in subsequent reactions to detect the target sequence. Such reactions may include hybridization to a labeled probe or unfolding of a fluorescently labeled secondary structure in a primer extension reaction.

It will further be appreciated that there are many alternatives to the fluorescently labeled secondary structure for detection of the displaced, extended detector oligonucleotide. That is, the secondary structure of the detector oligonucleotide is a convenient means for generating the signal in a homogeneous assay in "real-time" during target amplification. In other assay formats the displaced detector oligonucleotide may be detected directly or after being rendered double-stranded in a variety of ways, such as hybridization of a labeled probe or other methods known in the art. For example, it may be detected due to its increased size on gel electrophoresis, by hybridization to a labeled probe, by solid phase capture using a detector oligonucleotide-specific probe, by generation of a cleavable restriction endonuclease recognition site (see U.S. Pat. No. 5,550,025) or using other labeling and detection means known in the art.

EXAMPLE 1

SDA reactions were performed using amplification primers and hairpin-containing detector oligonucleotides designed to detect a region of the HIV-1 pol gene. The five detector oligonucleotides tested differed in the extent of their overlap with the right amplification primer. Overlaps were six nucleotides, seven nucleotides, five nucleotides and four nucleotides in length. In each case the overlap was such that, at the temperature of amplification, hybridization of detector and primer is competitive and mutually exclusive. All but one detector contained a single base mismatch with the target sequence. This was incorporated in order to overcome sequence heterogeneity in the pol gene among clinical isolates of HIV. SDA was carried out at 52° C. in the presence of either 0 or 250 copies of a cloned double-stranded DNA target sequence using 500 nM amplification primers, 50 nM bumper primers and 200 nM detector oligonucleotide. Detectors were fluorescently labeled with a donor/quencher dye pair (either Rhodamine/Dabcyl or Fluorescein/Dabcyl) separated by a BsoBI recognition sequence and were held in close proximity by a hairpin structure within the tail sequence as described in U.S. Pat. No. 5,919,630; U.S. Pat. No. 5,958,700 and the '869 Patent. Donor fluorescence was monitored during the course of the reaction.

For each detector oligonucleotide, donor fluorescence increased significantly during the course of the reaction when target DNA was present, indicating that the hairpin was unfolded and the restriction site was cleaved. In contrast, in the absence of target fluorescence remained consistently low throughout the reaction. To facilitate comparison between different detectors results were expressed in terms of the area under the curve or "MOTA". The greater the MOTA the more fluorescence generated and the more efficient the detection of amplified products. There was no statistically significant difference in MOTA between either of the two Rhodamine labeled detectors or among the three Fluorescein labeled detectors. The extent of overlap with the amplification primer, therefore, did not correlate with detection efficiency. Similarly, there was no correlation between detector performance and estimated melting temperature of the target binding sequence. The observation that a detector sequence with a single target mismatch which was otherwise identical to a detector sequence without the mismatch yielded similar results indicates that overlapping detectors are robust to single base mismatches within the target binding region.

EXAMPLE 2

SDA reactions containing between 0 and 250 copies of double-stranded target DNA were performed as in Example 1 using the Rhodamine/Dabcyl labeled detector oligonucleotide with the six nucleotide overlap with the right amplification primer. For comparison, parallel reactions were performed using a conventional non-overlapping detector. The MOTA scores obtained for both assay systems showed a significant increase as the level of target increased. The limit of detection (LOD) of these systems was calculated, defined as the input target level at which 95% of the reactions yielded a positive result. The LOD for the conventional detector was approximately 10 copies of input target regardless of the MOTA score selected as a cut-off for determining positivity. In contrast, the LOD for the overlapping detector was about 60–90 copies of input target per reaction, depending on the cut-off selected. These data demonstrate that detector oligonucleotides that overlap at the 5' end with the binding region of an upstream primer can be used for sensitive and reproducible detection of amplification products.

EXAMPLE 3

Overlapping detector oligonucleotides were designed for detection of a second region of the HIV-1 pol gene. In this system the central region of the amplicon that lies between the two amplification primers is highly heterogeneous, making it difficult to design a probe that will detect amplification products from a large number of strains of HIV. However, the overlapping detectors exploited sequence conservation in the hybridization region of the left amplification primer, thereby increasing the likelihood of detection of the majority of HIV genotypes. The 5' ends of the detector oligonucleotides overlapped the left amplification primer by eight, nine, ten, eleven, or twelve nucleotides, such that hybridization of the target binding sequences of the amplification primer and the detector oligonucleotide to this region is competitive and essentially mutually exclusive.

In order to test these oligonucleotide designs, SDA reactions were performed in the presence of 5,000 copies of double-stranded HIV target DNA. For comparison, control reactions employing a conventional detector oligonucleotide were also included. While the level of signal observed was significantly above the negative controls for all detectors, it did not correlate with the melting temperature of the detector hybridization region. However, higher MOTA scores were obtained from probes with shorter overlaps with the upstream amplification primer. Significantly, however, similar results were obtained with a conventional non-overlapping detector and the detector with the eight nucleotide overlap. These data indicate that overlapping detectors are capable of equivalent performance to conventional internal detectors.

What is claimed is:

1. A method for generating a signal indicative of the presence of a target sequence comprising:
    a) hybridizing a first oligonucleotide to the target sequence;
    b) generating a nickable restriction endonuclease recognition site comprising a second oligonucleotide hybridized to the target upstream from the hybridized first oligonucleotide, wherein the first and second oligonucleotides complete for hybridization to the target;
    c) nicking the restriction endonuclease recognition site and extending from the nick, thereby displacing the first oligonucleotide from the target sequence, and;
    d) detecting the displaced first oligonucleotide as an indication of the presence of the target sequence.

2. The method of claim 1 wherein the second oligonucleotide is an amplification primer.

3. The method of claim 1 which occurs during amplification of the target sequence.

4. The method of claim 1 wherein the nickable restriction endonuclease recognition site is generated in a target sequence amplification reaction.

5. The method of claim 4 wherein the nickable restriction endonuclease recognition site is generated by hybridization of an amplification primer to the target sequence.

6. The method of claim 1 wherein the first oligonucleotide comprises a secondary structure.

7. The method of claim 6 wherein the secondary structure is labeled.

8. The method of claim 7 wherein the displaced first oligonucleotide is detected by unfolding of the secondary structure.

9. The method of claim 8 wherein the secondary structure is a stem-loop structure.

10. The method of claim 8 wherein the secondary structure further comprises a restriction endonuclease recognition site which becomes cleavable or nickable in the detection step.

11. The method of claim 7 wherein the secondary structure is labeled with a fluorescent donor/quencher dye pair such that donor fluorescence is quenched prior to detection of the displaced first oligonucleotide.

12. A set of oligonucleotides for detecting a target sequence comprising:
   a) a first oligonucleotide comprising a nickable restriction endonuclease recognition site in single-stranded form and a target binding sequence capable of hybridizing to the target sequence, and;
   b) a second oligonucleotide comprising a target binding sequence which competes with the target binding sequence of the first oligonucleotide for binding to the target sequence.

13. The set of oligonucleotides of claim 12 wherein the first oligonucleotide is an amplification primer.

14. The set of oligonucleotides of claim 13 wherein the first oligonucleotide is an amplification primer for SDA.

15. The set of oligonucleotides of claim 12 wherein the second oligonucleotide further comprises a secondary structure.

16. The set of oligonucleotides of claim 15 wherein the secondary structure is labeled.

17. The set of oligonucleotides of claim 15 wherein the secondary structure further comprises a restriction endonuclease recognition site.

18. A method for detecting a nucleic acid target sequence comprising:
   a) hybridizing a first oligonucleotide and a second oligonucleotide to the target sequence, wherein the first and second oligonucleotides compete for hybridization to the target sequence, thereby generating a nickable restriction endonuclease recognition site upstream from the hybridized first oligonucleotide;
   b) nicking the restriction endonuclease recognition site and extending from the nick, thereby displacing the first oligonucleotide, and;
   c) detecting the displaced first oligonucleotide as an indication of the presence of the target sequence.

19. The method of claim 18 wherein the second oligonucleotide is an amplification primer and the first oligonucleotide is a detector oligonucleotide.

20. The method of claim 19 wherein the amplification primer and the detector oligonucleotide comprise target binding sequences which are at least partially identical.

21. The method of claim 19 wherein the displaced first oligonucleotide is detected by unfolding of a secondary structure in the first oligonucleotide.

22. The method of claim 21 wherein unfolding of the secondary structure is detected by a decrease in fluorescence quenching.

23. The method of claim 19 wherein the amplification primer is an amplification primer for SDA.

* * * * *